United States Patent [19]

Long et al.

[11] Patent Number: 4,547,078
[45] Date of Patent: Oct. 15, 1985

[54] METHOD AND DEVICE FOR MEASURING STEAM QUALITY

[75] Inventors: Stephen L. Long, Houston; Yin L. Cheung, Sugarland; Alfred Brown, Houston, all of Tex.

[73] Assignee: Texaco Inc., White Plains, N.Y.

[21] Appl. No.: 587,772

[22] Filed: Mar. 9, 1984

[51] Int. Cl.[4] .................... G01N 31/00; G01N 11/00
[52] U.S. Cl. ..................................... 374/42; 166/250
[58] Field of Search ............... 73/29, 61 R; 374/42; 236/20 R; 166/250; 436/38

[56] References Cited

U.S. PATENT DOCUMENTS

| | | | |
|---|---|---|---|
| 3,413,838 | 12/1968 | Duddy | 73/29 |
| 3,430,483 | 3/1969 | Clawson et al. | 73/29 |
| 3,499,488 | 3/1970 | Haynes, Jr. et al. | 166/250 |
| 3,596,516 | 8/1971 | Haynes, Jr. et al. | 73/29 |

Primary Examiner—David L. Lacey
Attorney, Agent, or Firm—Robert A. Kulason; James J. O'Loughlin; Fontaine C. Armistead

[57] ABSTRACT

Method and apparatus for obtaining a sample of the liquid component of steam and determining the quality of steam in a vessel or the like, such as steam flowing in a line used for steam injection in an oil well. The steam quality is determined by the known method of comparing the concentrations of dissolved solids in the liquid sample and the feedwater. A sample of the liquid phase of steam is trapped in a liquid vapor separator maintained at steam line temperature and pressure conditions. In this way errors due to condensation in the separator and its connecting lines are avoided. The sample is withdrawn from the separator into a collection chamber at a controlled rate which avoids reducing the pressure within the separator and thereby avoids the introduction of error because of erroneous concentration of dissolved solids within the separator sample. Errors are avoided also which in other methods and devices are introduced by the difficulty of obtaining representative two-phase samples and by deposition of solids in throttling orifices.

9 Claims, 2 Drawing Figures

METHOD AND DEVICE FOR MEASURING STEAM QUALITY

FIELD OF THE INVENTION

This invention concerns a method and apparatus for determining the quality of a liquid vapor mixture, i.e., the proportion of vapor in the liquid vapor mixture, and more particularly for determining the quality of saturated steam in a flow line to an injection well in a steam flooding project for oil recovery.

BACKGROUND OF THE INVENTION

In the operation of steam flooding to stimulate production of oil from oil reservoirs it is important to have a simple and accurate method to determine the quality of steam at the well head of an injection well. In such a stimulation process the amount of heat input to the reservoir determines the rate and amount of oil recovery, and heat input depends directly upon the steam quality. Steam that is generated for injection into the reservoir arrives at the well head as saturated or wet steam, i.e., a mixture of vapor and liquid, at super-atmospheric pressure. The greater the proportion of vapor in that mixture, i.e., the greater the steam quality, the more the heat input to the reservoir. Steam quality thus directly affects the rate and the ultimate amount of recovery of oil, and therefore has a bearing upon earnings and investment requirements.

Various methods have been used for determining steam quality in saturated steam lines with varying degrees of accuracy and simplicity of operation. One such method extracts a sample of steam from the steam line through a throttling orifice, separates the liquid from the vapor in a separator vessel, compares the salt concentrations in the liquid portion of the sample and in the feedwater to the steam generator, and solves equations relating the steam quality to those salt concentrations and to enthalpy values (from steam tables) for the liquid and vapor components of steam. In that method, which is described in U.S. Pat. Nos. 3,499,488, 3,596,516, and 3,550,849, assigned to the same assignee as this application, the physical separation of liquid and vapor occurs in a separator off to the side of the steam line with the resulting possibility of condensation within the separator under cold and windy ambient conditions. Such condensation invalidates the assumptions on which the method is based, thus compromising the accuracy of the measurement. Additionally in using the above described method it is difficult to get a consistently representative sample because of the complex nature of two-phase flow, and also problems arise from the deposition of dissolved solids in the throttling orifice. One such problem is that the sample so derived has an erroneously low concentration of dissolved solids; another problem is that the deposited solids tend to plug the orifice.

BRIEF SUMMARY OF THE INVENTION

In this invention a sample of the liquid phase of the super-atmospheric saturated steam is separated from the vapor phase by trapping the liquid in a liquid vapor separator that is maintained at steam line pressure and temperature. In this way condensation within the separator, such as occurs when the separator is at lower pressure and temperature, is avoided.

A portion of the separated liquid sample is then withdrawn into a collection chamber in a manner which prevents the super-atmospheric pressure of the steam in the liquid-vapor separator from being reduced substantially. If such a reduction in pressure within the separator were allowed to happen it would result in a flashing of vapor from the collected separator sample, with a resulting error in concentration of dissolved solids within the separator sample. The collected sample within the collection chamber is then allowed to cool to ambient temperature and is removed for measurement of the concentration of dissolved solids. The concentration of dissolved solids in the withdrawn sample is compared with the concentration of dissolved solids in the feedwater to the steam generator, and the quality of the steam within the steam line can be determined by equation (4) derived in the next paragraph.

Feedwater containing $W_{LF}$ lbs water and $W_S$ lbs salt are converted by the steam generator to steam consisting of $W_V$ lbs vapor, $W_L$ lbs liquid, and $W_S$ lbs salt. Expressed as an equation this is $$W_{LF} + W_S = W_V + W_L + W_S \tag{1}$$

Define salt concentration in feedwater, $$C_F = W_S/W_{LF} \tag{2}$$

Define salt concentration in liquid phase of steam, $$C_S = W_S/W_L \tag{3}$$

Define quality of steam, $$X_S = W_V/(W_V + W_L) = (W_{LF} - W_L)/W_{LF} = 1 - W_L/W_{LF}$$

whence $$X_S = 1 - C_F/C_S \tag{4}$$

While equation (4) is expressed in terms of salt concentrations it will readily be seen that it is equally applicable to concentrations of any dissolved solids in the feedwater and in the liquid phase of the steam. Equation (4) is well known and is employed in the three prior art patents cited above.

Two methods and devices are illustrated for accomplishing the necessary slow withdrawal of liquid sample from the separator to the collection chamber. In one method a suction device is employed including a chamber having a piston movable therein under the constraint of mechanical means through which the piston's rate of motion within the chamber can be made slow enough so that the super-atmospheric pressure within the separator remains substantially unchanged during the withdrawing of a sample into the collection chamber.

In the other method a collection chamber which is filled with a liquid to be displaced is used. A vent from this collection chamber contains a regulating valve, by cracking of which it is possible to allow the displaceable liquid within the collection chamber to be slowly displaced by the liquid sample flowing from the liquid vapor separator. Once again this rate of flow is controlled to be slow enough so that no appreciable change in pressure occurs within the liquid vapor separator inside the steam line.

The objections named above to another method of measuring line steam quality are overcome in this invention as follows. The problem with condensation in the liquid vapor separator does not exist in the present invention since the separator is in communication with or is within the steam line and therefore is always at steam line pressure and temperature. Also there is no problem associated with the difficulty of getting consistently representative samples of two phases since in this invention only the liquid phase is collected. Further there is no problem with deposition of solids in a throttling orifice since no throttling orifice is used.

Accordingly, it is a principal object of this invention to eliminate error introduced into steam quality measurements by condensation within the liquid vapor separator and lines connected thereto.

Another object is to obtain a consistently representative sample from which steam quality can be reliably determined.

Another object is to avoid errors in measurement of steam quality caused by deposition of solids in a throttling orifice.

BRIEF DESCRIPTION OF THE DRAWINGS

The foregoing and other objects and benefits of the invention will be more fully set forth below in connection with the best mode contemplated by the inventors of carrying out the invention, and in connection with which there are illustrations provided in the drawings, wherein.

DESCRIPTION OF THE PREFERRED EMBODIMENT

As pointed out above there have been steam quality measurement problems in steam flooding projects where steam is injected into oil wells in order to stimulate the recovery of additional oil by the heating effects of the steam. One such problem arises from condensation of the steam in the line to the conventional external liquid vapor separator and in the separator itself due to extremely cold and windy ambient conditions thus comprising the accuracy of the measurement. Other problems are associated with obtaining consistently representative samples because of the complex nature of two-phase flow, and with deposition of dissolved solids in the throttling orifice.

The method according to this invention provides for a simple and effective procedure that permits measurement of steam quality in a flow line in a way that overcomes the above objections.

Figure 1:
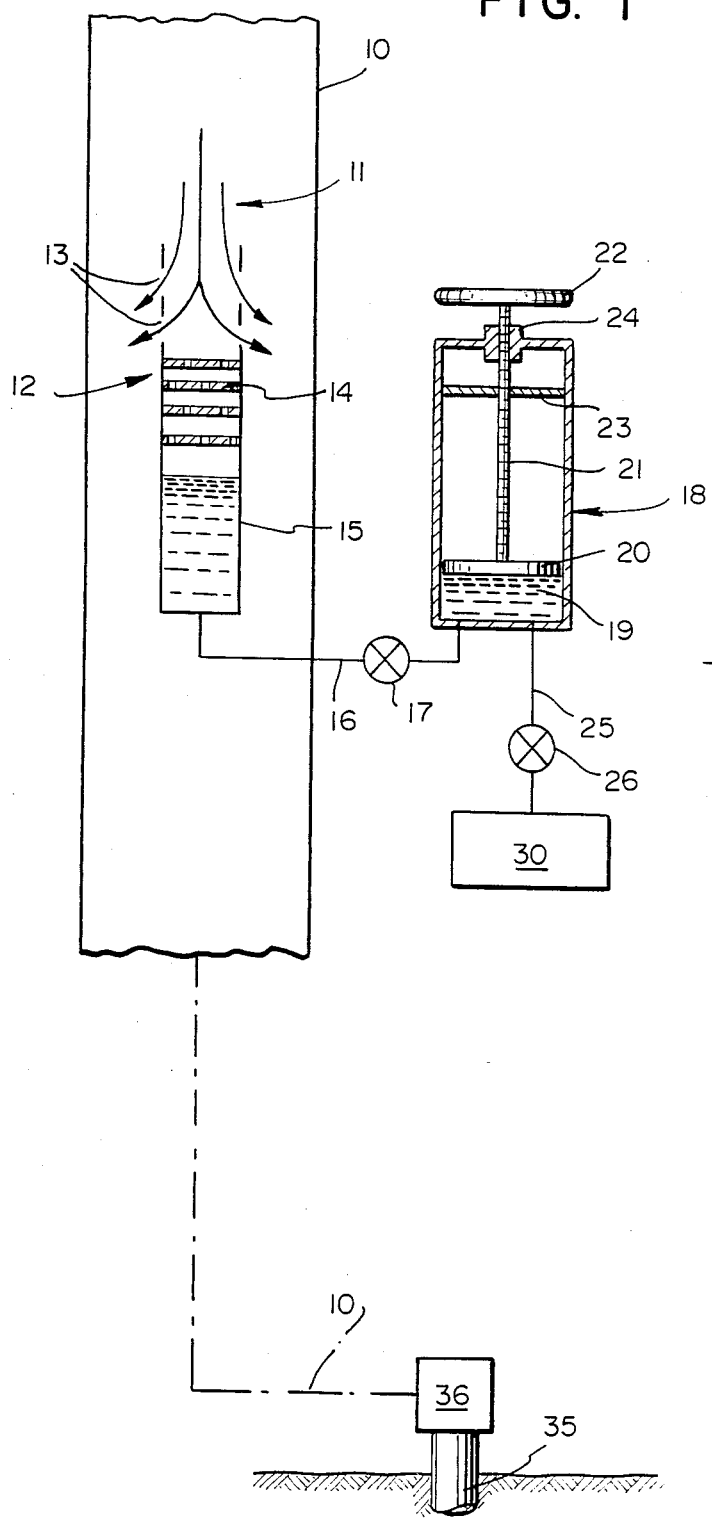
FIG. 1 of the drawings is a schematic representation of a steam flow line together with elements that are employed in order to carry out the method according to the invention, including as one such element an embodiment of a collection chamber by means of which a sample is withdrawn from the liquid vapor separator.

FIG. 1 depicts one embodiment of this invention wherein saturated steam at super-atmospheric pressure for injection into well 35 is flowing in steam line 10 toward well 35, having a well head 36. A liquid vapor separator 12 resides within steam line 10 so that the separator and its contents are at all times at steam line conditions of temperature and pressure. In this way the sample of steam liquids which is collected in separator 12 is truly representative of the liquid content of the steam flow and does not include a false indication resulting from condensation of steam vapor in the separator such as in previous devices. Steam flowing within steam line 10 is shown by flow lines 11 entering separator 12 and emerging through vapor vents 13. Baffles 14 cause the droplets of liquid phase within the steam flow to fall out of the flowing steam and to collect in the lower portion of the separator 12 as separator liquid sample 15.

There is a separator sample withdrawal conduit 16 containing a valve 17 which connects separator 12 with a collection chamber 18. Collection chamber 18 is designed to operate on a suction principle in order that a portion of separator liquid sample 15 can be drawn at a carefully controlled rate through conduit 16 into collection chamber 18 so gradually that no perceptible change occurs in the pressure within separator 12. This gradual rate of withdrawal of sample is effected by movable piston 20 within collection chamber 18 which piston has a threaded piston rod or shaft 21. Threaded rod 21 engages threaded cap 24 at the upper closure of collection chamber 18 and is topped by handwheel 22. Piston rod 21 has threads designed to be in effect self-locking so that piston 20 moves only when handwheel 22 is turned. Rotation of handwheel 22 causes piston 20 to move vertically at a controllable rate within collection chamber 18. Chamber 18 also includes high temperature packing material 23 as packing around piston rod 21.

When it is desired to withdraw a portion of separator liquid sample 15 from liquid vapor separator 12, valve 17 is opened and piston handle 22 is rotated at a controlled rate such that piston 20 moves upward gradually within collection chamber 18, and a portion of separator liquid sample 15 is drawn over through conduit 16 into the collection chamber 18. The drawn over liquid sample is shown within collection chamber 18 as collection chamber liquid sample 19.

This withdrawal of sample is done slowly in order to avoid any appreciable pressure drop within separator 12. If the pressure were allowed to drop appreciably within separator 12 any collected sample 15 would flash some of its liquid to vapor, which would escape from separator 12 with the result that the remaining sample 15 would then have a greater concentration of dissolved solids or salts than it initially had, and therefore the ultimate reading of the device would be thrown off.

When a sufficient liquid sample 19 has been transferred, valve 17 is closed, collection chamber 18 is allowed to cool down to ambient temperature, and valve 26 in collection chamber withdrawal conduit 25 is opened, allowing sample 19 to be removed into measuring means 30 for measuring the concentration of dissolved solids in sample 19. This measured concentration is $C_S$ of equation (4). $C_F$ for the feedwater is either predetermined or is measured by means similar to means 30, and quality $X_S$ is determined by use of equation (4).

Figure 1A:
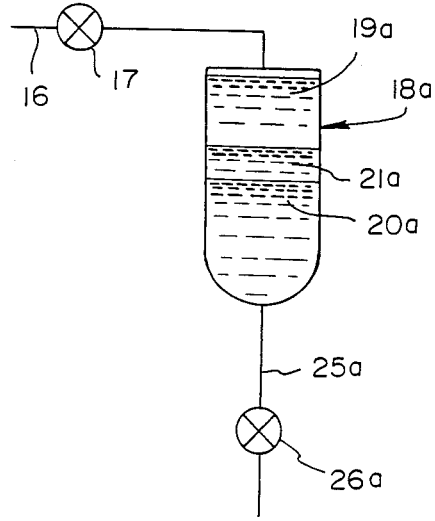
FIG. 1a shows an alternate embodiment of the collection chamber.

FIG. 1a shows an alternate embodiment to collection chamber 18 as indicated by collection chamber 18a. Collection chamber 18a is initially filled with a liquid 20a. Separator sample withdrawal conduit is again shown as 16 with separator sample withdrawal valve 17 in its line. In this embodiment the sample is withdrawn from separator 12 through separator sample withdrawal conduit 16 by allowing sample 15, which is at the super-atmospheric pressure of steam line 10, to displace from collection chamber 18a the liquid 20a which fills collection chamber 18a at the start. Liquid 20a is preferably deionized water, so that no dissolved solids will be introduced into sample 19a by contact between 19a and 20a. There is a collection chamber withdrawal conduit or vent 25a from collection chamber 18a with collection chamber withdrawal valve 26a in its line. Valve 26a is a regulating valve which when cracked slightly open will allow the displaceable liquid 20a which initially fills collection chamber 18a to be driven from collection chamber 18a by the flow of separator liquid sample 15 through separator sample withdrawal conduit 16 into the upper portion of collection chamber 18a. This inflowing sample is indicated in FIG. 1a at 19a. There is a mixing zone indicated at 21a where some of the inflowing sample 19a mixes with some of the displaceable liquid 20a. When all of the displaceable liquid 20a is displaced spewing will occur as the sample which is at saturation temperature will flash into vapor at atmospheric pressure. A little of this vapor should be flashed in order to purge the mixing zone 21a. Then both valves 17 and 26a are closed, and the chamber is allowed to come to ambient conditions. Once again, as in the case of collection chamber 18 in FIG. 1, when ambient conditions are reached collected sample 19a within collection chamber 18a can be withdrawn through valve 26a, and the concentration of the dissolved solids in the liquid sample, $C_S$ can be measured for use together with the predetermined or measured concentration $C_F$ to obtain steam quality $X_S$ by equation (4).

It will be readily seen that still other embodiments of collection chamber are possible. For example, the mixing zone 21a in FIG. 1a might be replaced by a free floating piston, in which case the collection chamber would need to be provided with a vent valve and a sampling valve for taking the desired sample. In another embodiment piston 20 of FIG. 1 might be replaced by having collection chamber 18 initially filled with oil and drawing the sample under control of a top-mounted regulating valve in the manner that regulating valve 26a is used in the embodiment of FIG. 1a.

While particular embodiments of the invention have been described above in accordance with the applicable statutes this is not to be taken as in any way limiting the invention but merely as being descriptive thereof. All such embodiments are intended to be included within the scope of the invention which is to be limited only by the following claims.

We claim:

1. A method for obtaining an indication of the quality of saturated steam which occupies a vessel or steam line, said steam having liquid and vapor components and being at super-atmospheric pressure, said saturated steam being generated from feedwater having a predetermined solids content, which method comprises
    obtaining a sample of the liquid component of said saturated steam at said super-atmospheric pressure,
    withdrawing at least a portion of said liquid sample in a manner which prevents the super-atmospheric pressure of said saturated steam from changing substantially,
    determining the solids content of said withdrawn liquid sample, and
    comparing the solids content of said withdrawn liquid sample with said predetermined solids content of said feedwater and thereby obtaining an indication of the quality of said saturated steam.

2. The method of claim 1 wherein said solids are salt and said predetermined solids content and determined solids content are respectively a predetermined salt content and a determined salt content.

3. In a steam injection procedure for recovering oil by introducing steam through a steam line into one or more injection wells, a method for determining the quality of saturated super-atmospheric pressure steam in said steam line, said saturated steam having liquid and vapor components and being generated from feedwater having a predetermined concentration of solids, which method comprises:
    obtaining a sample of the liquid component of said saturated steam at said super-atmospheric pressure,
    withdrawing at least a portion of said liquid sample in a manner which prevents the super-atmospheric pressure of said saturated steam from changing substantially,
    determining the concentration of solids in said withdrawn liquid sample, and
    obtaining the quality of said saturated steam from the equation $X_S = 1 - (C_F/C_S)$,
    where
    $X_S$ is the saturated steam quality,
    $C_F$ is said predetermined concentration of solids in the feedwater, and
    $C_S$ is said determined concentration of solids in the withdrawn liquid sample.

4. Apparatus for determining the quality of saturated steam which occupies a vessel or steam line, said steam having liquid and vapor components at super-atmospheric pressure and having been generated from feedwater having a predetermined solids content, comprising in combination:
    means for obtaining a sample of the liquid component of said saturated steam at said super-atmospheric pressure,
    means for withdrawing at least a portion of said liquid sample at a controlled slow rate such that the super-atmospheric pressure of said saturated steam does not change substantially, and
    means for determining the solids content of said withdrawn liquid sample, said quality of saturated steam being functionally related to said determined solids content of said withdrawn liquid sample and said predetermined solids content of said feedwater by a known equation.

5. Apparatus for determining the quality of saturated steam which occupies a vessel, said steam having liquid and vapor components at super-atmospheric pressure and having been generated from feedwater having a predetermined solids content, comprising in combination:
    means communicating with said vessel and maintained in temperature equilibrium with said saturated steam occupying said vessel for obtaining a sample of the liquid component of said saturated steam at super-atmospheric pressure,
    means for withdrawing at least a portion of said liquid sample at a controlled slow rate such that the super-atmospheric pressure of said saturated steam does not change substantially, and
    means for determining the solids content of said withdrawn liquid sample, said quality of saturated steam being functionally related to said determined solids content of said withdrawn liquid sample and said predetermined solids content of said feedwater by a known equation.

6. Apparatus for determining the quality of saturated steam which occupies a steam line, said steam having liquid and vapor components at super-atmospheric pressure and having been generated from feedwater having a predetermined solids content, comprising in combination:

means located within said steam line and at least partially surrounded by saturated steam for obtaining a sample of the liquid component of said saturated steam at said super-atmospheric pressure, means for withdrawing at least a portion of said liquid sample at a controlled slow rate such that the super-atmospheric pressure of said saturated steam does not change substantially, and means for determining the solids content of said withdrawn liquid sample, said quality of saturated steam being functionally related to said determined solids content of said withdrawn liquid sample and said predetermined solids content of said feedwater by a known equation.

7. Apparatus as in claim 6 wherein said means for withdrawing at least a portion of said liquid sample includes a suction device comprising an expandable chamber controllable as to its rate of expansion so that said rate can be made slow enough that super-atmospheric pressure of said saturated steam remains substantially unchanged during the withdrawing of said at least a portion of said liquid sample.

8. Apparatus as in claim 7 wherein said means for withdrawing at least a portion of said liquid sample includes a piston movably positioned in said chamber and means for constraining the motion of said piston such that said piston's rate of motion within said chamber can be made slow enough that said super-atmospheric pressure of said saturated steam remains substantially unchanged during the withdrawing of said at least a portion of said liquid sample.

9. Apparatus as in claim 6 wherein said means for withdrawing at least a portion of said liquid sample includes a liquid displacement device filled with a liquid to be displaced by said at least a portion of said liquid sample, said displacement device having a regulating valve in a vent therefrom, such that opening said regulating valve a controllably small amount initiates said withdrawing of at least a portion of said liquid sample at a rate slow enough that said super-atmospheric pressure of said saturated steam remains substantially unchanged during the withdrawing of said at least a portion of said liquid sample.

* * * * *